United States Patent
Yoshida et al.

(10) Patent No.: US 12,246,109 B2
(45) Date of Patent: Mar. 11, 2025

(54) REGENERATION OF TENDON AND TENDON SHEATH, RESTORATION MATERIAL, AND USE OF RESTORATION MATERIAL

(71) Applicants: Toshiko Yoshida, Toyama (JP); Motonori Okabe, Toyama (JP); Ryusuke Osada, Toyama (JP); Mineyuki Zukawa, Toyama (JP); SAKURA SEIKI CO., LTD., Nagano (JP)

(72) Inventors: Toshiko Yoshida, Toyama (JP); Motonori Okabe, Toyama (JP); Ryusuke Osada, Toyama (JP); Mineyuki Zukawa, Toyama (JP); Masahiko Arakawa, Nagano (JP)

(73) Assignees: Toshiko Yoshida, Toyama (JP); Motonori Okabe, Toyama (JP); Ryusuke Osada, Toyama (JP); Mineyuki Zukawa, Toyama (JP); SAKURA SEIKI CO., LTD., Nagano (JP)

( * ) Notice: Subject to any disclaimer, the term of this patent is extended or adjusted under 35 U.S.C. 154(b) by 1065 days.

(21) Appl. No.: 17/257,918

(22) PCT Filed: Aug. 30, 2019

(86) PCT No.: PCT/JP2019/034052
§ 371 (c)(1),
(2) Date: Jan. 5, 2021

(87) PCT Pub. No.: WO2020/045608
PCT Pub. Date: Mar. 5, 2020

(65) Prior Publication Data
US 2021/0283306 A1    Sep. 16, 2021

(30) Foreign Application Priority Data
Aug. 30, 2018  (JP) .................................. 2018-174244

(51) Int. Cl.
*A61L 27/36*    (2006.01)

(52) U.S. Cl.
CPC ....... *A61L 27/3604* (2013.01); *A61L 27/3662* (2013.01); *A61L 27/3691* (2013.01); *A61L 2430/10* (2013.01)

(58) Field of Classification Search
CPC ............ A61L 27/3604; A61L 27/3662; A61L 27/3691; A61L 2430/10; A61L 2430/40
See application file for complete search history.

(56) References Cited

U.S. PATENT DOCUMENTS

| | | | |
|---|---|---|---|
| 5,612,028 A | 3/1997 | Sackier et al. | |
| 8,414,929 B2 | 4/2013 | Nikaido et al. | |
| 8,932,641 B2 | 1/2015 | Nikaido et al. | |
| 2007/0105113 A1 | 5/2007 | Sagawa et al. | |
| 2009/0258082 A1 | 10/2009 | Nikaido et al. | |
| 2010/0098743 A1* | 4/2010 | Nikaido | A61P 43/00 424/424 |

FOREIGN PATENT DOCUMENTS

| | | |
|---|---|---|
| JP | S63260549 | 10/1988 |
| JP | H10113384 | 5/1998 |
| JP | 2007-54015 | 3/2007 |
| WO | WO-0059490 | 10/2000 |

OTHER PUBLICATIONS

Jay (Initial Clinical Experience with the Use of Human Amniotic Membrane Tissue During Repair of Posterior Tibial and Achilles Tendons, AFcell Medical, 2009). (Year: 2009).*
Liu (Experimental study of tendon sheath repair via decellularized amnion to prevent tendon adhesion, PLoS ONE, 2018 (Year: 2018).*
International Search Report for PCT/JP2019/034052 dated Sep. 30, 2019.
Rahmadian, et al, "The effects of lyophilized amniotic membrane in the prevention of peritendinous adhesion after achilles tendon repair in rabbit", Aug. 8, 2014, p. 43, Journal of Japanese Society of Tissue Transplantation, vol. 13, No. 1.
Okabe, et al, "Adhesion prevention effect of hyper dry human dry amniotic membrane (HD amniotic membrane) in tendon rupture repair model", Mar. 27, 2019, p. 216, the 124th Annual Meeting of Japanese Association of Anatomists, National Academic Meeting Lecture Program / Abstracts).

(Continued)

*Primary Examiner* — Robert A Wax
*Assistant Examiner* — John Seungjai Kwon
(74) *Attorney, Agent, or Firm* — Stephen J. Weyer, Esq.; Stites & Harbison, PLLC

(57) ABSTRACT

An object is to provide a dried amniotic membrane that promotes regeneration of a tendon and a tendon sheath when a tendon injury has occurred and that reduces loss of the motor function of fingers of upper limbs and lower limbs due to tendon adhesion as a novel regeneration material. As a means for resolution, a dry amniotic membrane is produced by performing a specific drying treatment, that is, during a depressurization operation in which a fresh amniotic membrane placed in a treatment tank is continuously heated by an infrared heater provided in the treatment tank, and the inside of the treatment tank is brought into a depressurized state; and a pressure recovery operation in which the pressure of the inside of the treatment tank in a depressurized state is raised slightly toward the atmospheric pressure, drying is performed while applying energy to water molecules present in the amniotic membrane by irradiating the fresh amniotic membrane with a microwave also from a microwave generator provided in the treatment tank. The dried amniotic membrane retaining of the cell and tissue structures by repeating the treatment of drying a plurality of times promotes regeneration of the motor function of fingers of upper limbs and lower limbs after tendon suture surgery and is useful as a regeneration material.

3 Claims, 3 Drawing Sheets

(56) References Cited

OTHER PUBLICATIONS

Office Action dated Nov. 8, 2022 in Chinese Application No. 2019-80054757.X.
Wen, et al, "Study of Wrist Injury Therapy", 2$^{nd}$ ed., (Mar. 2018) SPM, pp. 114-119.
First Office Action dated Dec. 17, 2021 in Chinese Application No. 201980054757.X.
Gao, et al, "Experimental Study on Human Amniotic Membrane for Repairing Tendon Sheath Defect", Mar. 2013, pp. 335-339, vol. 27, No. 3, Chinese Journal of Reparative and Reconstructive Surgery.
Supplementary European Search Report dated Aug. 17, 2021 in European Application No. 19855230.9.
Office Action dated Jul. 19, 2022 in Japanese Application No. 2020-539618.
Iitsuka, et al, "Characteristic of postoperative treatment after repair of flexor tendon rupture in Zone II", 2006, vol. 6, No. 1, Health Study Journal of Hiroshima University.

\* cited by examiner

REGENERATION OF TENDON AND TENDON SHEATH, RESTORATION MATERIAL, AND USE OF RESTORATION MATERIAL

TECHNICAL FIELD

The present invention relates to regeneration and restoration of a tendon and a tendon sheath, and more particularly relates to a dry amniotic membrane produced by a specific drying method as a medical material to be used for regeneration and restoration of a tendon and a tendon sheath.

BACKGROUND ART

An amniotic membrane is a tough biological membrane constituted by collagen and elastic fibers, and utilization thereof as a material for repairing the bladder, urethra, or ureter (PTL 1) and a membrane substitute for the cerebral dura mater, pericardium, or the like including a laminate composed of a sheet-like porous intermediate agent between two layers of collagen membrane derived from an amniotic membrane (PTL 2) have been proposed.

An amniotic membrane hardly causes rejection in transplantation, and has an anti-inflammatory effect and a wound repair accelerating effect, and has been used as dressing materials for skin burn injury, repair of umbilical hernia, an artificial vagina, prevention of adhesion in abdominal surgery, or the like.

Recently, an amniotic membrane is also used for regeneration of the cornea, esophagus, trachea, blood vessel, skin, tympanic membrane, or the like, when an amniotic membrane is used, generally a frozen amniotic membrane is used. Further, it has been reported that a cryopreserved amniotic membrane contained immune compatibility can be utilized for restoration of a tendon (PTL 3). On the other hand, a frozen amniotic membrane had a problem for storage stability (about 3 months at −80° C.), that is freezing and thawing system are complicated, and so on. To solve such a problem, a new method which dried with a specific drying treatment has been proposed (PTL 4).

CITATION LIST

Patent Literature

PTL 1: JP-A-63-260549
PTL 2: JP-A-10-113384
PTL 3: WO 2015/17144
PTL 4: JP-A-2007-54015

SUMMARY OF INVENTION

Technical Problem

A tendon keeps to be able smooth movement of bones with a high gliding property. However, after traumatic injury or surgery, a tendon easily adheres to a surrounding tissue to cause joint contracture. Various attempts for preventing tendon adhesion have been made. For example, it has been reported that the immune compatibility contained in a cryopreserved amniotic membrane is utilized for restoration of a tendon after frozen amnion was thawed (PTL 3).

In a medical treatment for tendon rupture, maintenance of joint range of motion of limbs has been required for reducing aftereffects.

Solution to Problem

A dried amniotic membrane produced by a specific drying treatment is considered to have the same anti-inflammatory effect, infection inhibitory effect, and epithelialization accelerating effects as same as a cryopreserved amniotic membrane. These characteristics has a rule in guiding accelerating wound healing, and a tendon sheath regeneration was promoted. Therefore, prevention of tendon adhesion and healing a bone injury generally occurs after a tendon injury and ruptured can be expected. In consequence, regeneration promotion effect, and further, promotion of healing at a bone injury site part from a ruptured tendon can be expected. That is, regeneration of the motor function of fingers of upper limbs and lower limbs can be expected.

The present inventors found out that a disorder such as adhesion is suppressed and regeneration of motor function is promoted by using a dried amniotic membrane itself produced by a specific drying treatment as a medical treatment for a lost or injured tendon sheath. Then it was accomplished the present invention.

Advantageous Effects of Invention

The medical treatment for a tendon and a tendon sheath injury using an HD (Hyper-Dry) amniotic membrane dried by a special method which is easy and good operability when it was used medical treatment, and is able to keep the characteristics of amnion membrane are not only restoration and regeneration of a tendon and a tendon sheath, but also reduction of adhesion at a site surrounding a sutured tendon. Moreover, healing at a bone injury site is also promoted. By using an HD amniotic membrane, the regeneration of a tendon sheath accompanied with a bone fracture and suppressing adhesion involving a bone are possible to build bone formation normally. As a result, the QOL of a patient is improved.

DESCRIPTION OF EMBODIMENTS

Figure 1:
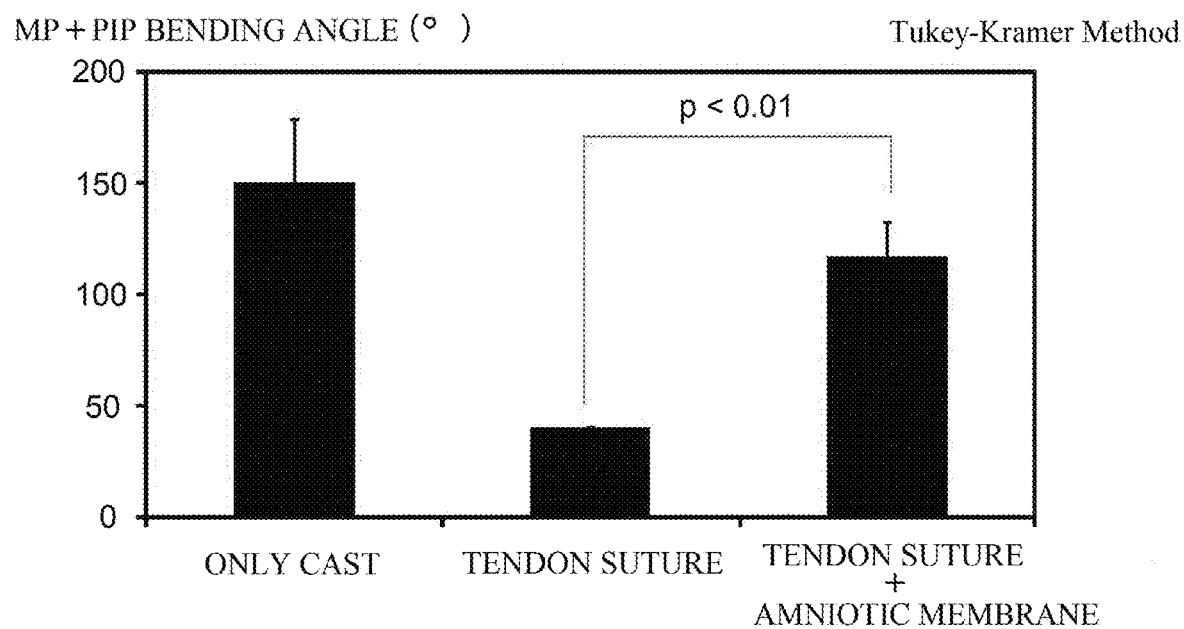
FIG. 1 is a view of measurement results of joint range of motion (ROM).

A dried amniotic membrane produced by a specific drying treatment is, for example, a dried amniotic membrane described in PTL 1 (hyper-dry amniotic membrane, hereinafter referred to as HD amniotic membrane). That is, during a depressurization operation, a fresh amniotic membrane placed in a treatment tank is continuously heated by an infrared heater provided. The pressure of the treatment tank is adjustment from a depressurized state to the atmospheric pressure repeatedly. During then, irradiated microwave from a microwave generator with treatment tank is drying the water molecule by applying energy. By these repeating processes, the amniotic cells are dried up, but the cell can be retained and keep structure of amniotic membrane.

A tendon is tough tissue which composed of fibers, and connecting a muscle with a bone. Particularly, a flexor tendon connecting a finger to a forearm is very important to movement of fingers and wrist. There are a finger flexor tendon which allows a finger to bend, and a radial carpal flexor tendon, an ulnar carpal flexor tendon, and a palmaris longus muscle tendon which allow a hand joint to bend. These flexor tendons run through a tendon sheath which composed of two area, one is a tough fibrous portion called a ligamentous tendon sheath, and a soft membranous tendon sheath. Ligament tendon was working not to be detached from a bone. The tendon in the present invention includes the above-mentioned tendons and tendon sheaths.

When the flexor tendon is partially ruptured due to a traumatic injury, a sport, or the like, generally, a conservative treatment is possible and cast fixation is performed. In the case of complete rupture, suture surgery is needed. Adhesion sometimes occurs after tendon suture surgery; therefore, the tendon adhesion in the present invention means adhesion occurring after tendon suture surgery.

When the HD amniotic membrane of the present invention is used for restoration of a tendon, for example, an HD amniotic membrane with an appropriate size may be patched around a ruptured tendon and/or tendon sheath.

<Therapeutic Effect on Model Animal>

The toe flexor tendon of a rabbit at 12 weeks of age was ruptured at the proximal phalanx level, and thereafter sutured, and then, cast fixation was performed for 4 weeks, and 48 toes were classified into 3 groups, respectively. The classification was performed into a group in which an HD amniotic membrane was wrapped around the sutured site after suturing the tendon (+HD amniotic membrane group), a group in which only the tendon was sutured (tendon suture group), and an untreated group (control group). A mechanical test, microscopic evaluation, and histological evaluation were performed.

Note that for the handling of the experimental animals, the guideline of National Institutes of Health was followed, and approval was obtained from the Animal Experiment Committee of the University of Toyama. Further, the experiment was performed according to the guideline of the Animal Experiment Committee of the University of Toyama.

<Method 1> Measurement of Joint Range of Motion

General anesthesia is performed to euthanasia, and took the toes of each groups for samples. The proximal phalanx of the collected toe was fixed to a measuring table, and the join range of motion (ROM) was measured by moving the toe tip in the bending direction and the extending direction.

When the join range of motion (ROM) was quantitatively measured by pulling the tendon, the range of motion was significantly larger in the group treated by using the HD amniotic membrane (+HD amniotic membrane group) than in the positive control (tendon suture group) (FIG. 1).

<Method 2> Histological (Adhesion) Evaluation

HE staining and immunostaining were performed, and the relationship an HD amniotic membrane with a rabbit tendon sheath tissue, and the distribution of immunostaining positive cells were histologically analyzed. By the observation, evaluation for a morphological change in the tendon itself and fibrous adhesion to the surrounding at the same time as regeneration of the tendon sheath could be performed.

Figure 2:
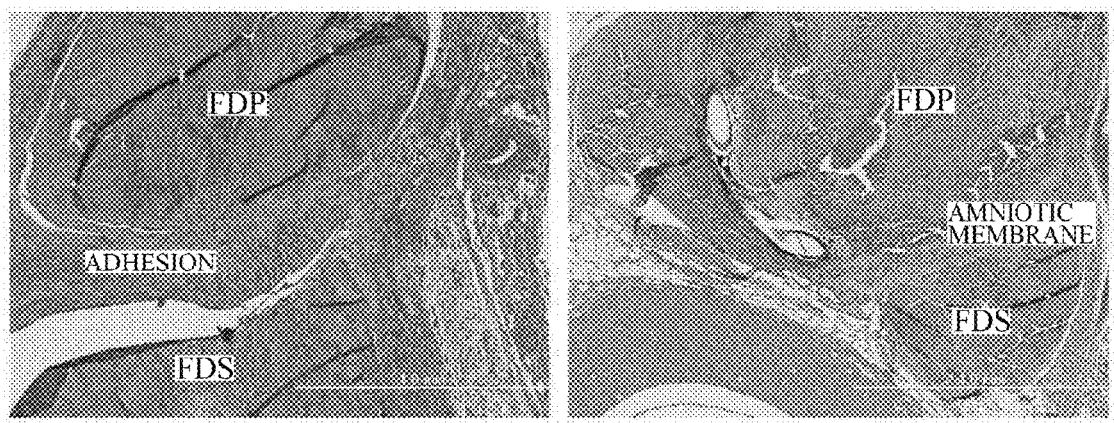
FIG. 2 is a view histologically showing a structure of an HD amniotic membrane and a rabbit tendon sheath tissue, and a distribution of immunostaining positive cells.

As a result, when the adhesion around the tendon tissues between the deep digital flexor tendon and the superficial digital flexor tendon was morphologically examined, no adhesion was observed in the group using the HD amniotic membrane (FIG. 2).

<Method 3> Measurement of Pull-Out Strength (Degree of Adhesion)

The flexor tendon is cut at a more proximal site (MTP site) than the sutured site in the collected toe. The proximal phalanx of the toe is fixed to a traction strength measuring tester in advance, and the distal phalanx to which the tendon at the distal side adheres is grasped by a traction clamp and pulled at a constant speed. In this manner, the strength when the tendon is pulled out is measured, and the degree of adhesion is reflected in the pull-out strength. That is, the tendon was pulled from the fixed toe at a constant speed, and the adhesion strength was dynamically evaluated.

Figures 3, 4:
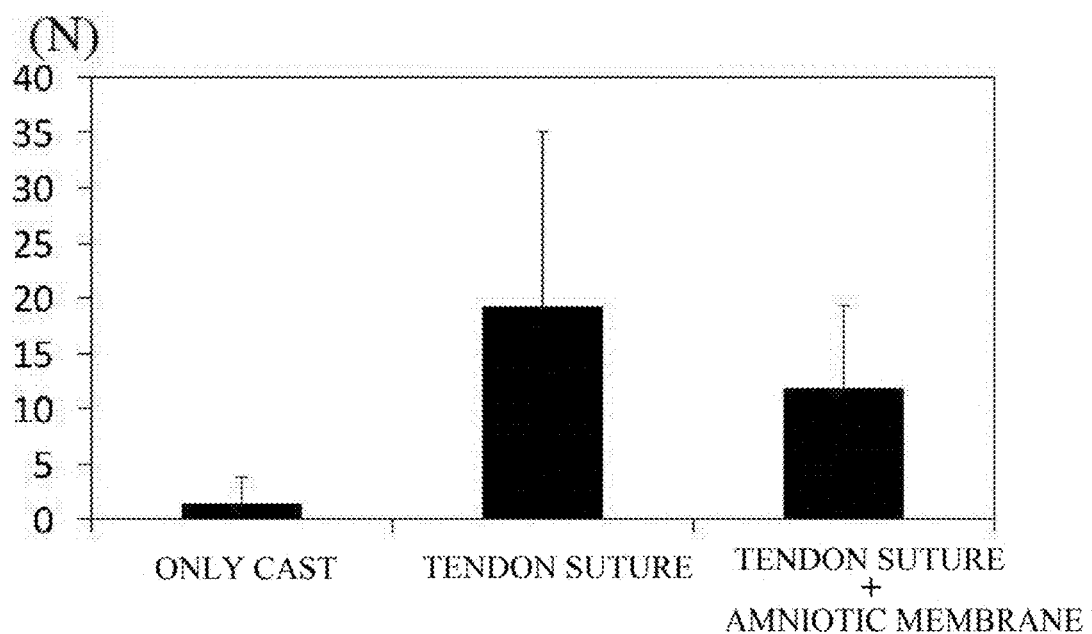
FIG. 3 is a view of results of a tendon pull-out test by a tensile test.
FIG. 4 is a view showing results of an adhesion rating test.

As a result, a necessary tension when pulling out the tendon was smaller in the group treated using the HD amniotic membrane (+HD amniotic membrane group) than in the positive control (tendon suture group) (FIG. 3).

<Method 4> Evaluation of Adhesion Between Bone and Tendon (Adhesion Rating Test)

The collected toes were scored for the degree of adhesion under a stereoscopic microscope by the following evaluation generally used in the field of orthopedic surgery.

0 point: normal: slippery surface
1 point: easy to glide: the presence of inclusions that do not interfere with tendon gliding
2 points: blunt peeling: can be detached using tweezers
3 points: sharp peeling: can be detached by incision using a surgical knife In the adhesion rating test, the group treated using the amniotic membrane (+HD amniotic group) showed a value significantly closer to that of the control (control group) than the positive control (tendon suture group) (FIG. 4).

<Method 5> Evaluation of Safety for Healing of Fracture that Often Occurs Simultaneously with Tendon Rupture Clinically, a finger traumatic injury is often accompanied bone fracture with causing tendon rupture. It is necessary to confirm that the HD amniotic membrane which promotes regeneration of a tendon sheath does not adversely affect bone formation at the fracture site from the viewpoint of safety of the medical treatment. Therefore, a model with an incomplete fracture in which a bone defect was caused on the surface in contact with the flexor tendon of the phalange was created, and a group in which a dry amniotic membrane was placed between this surface and the flexor tendon to close the wound, and a group in which the wound was closed without placing anything were prepared, and it was examined whether a difference in bone formation as seen by XP occurs.

Figure 5:
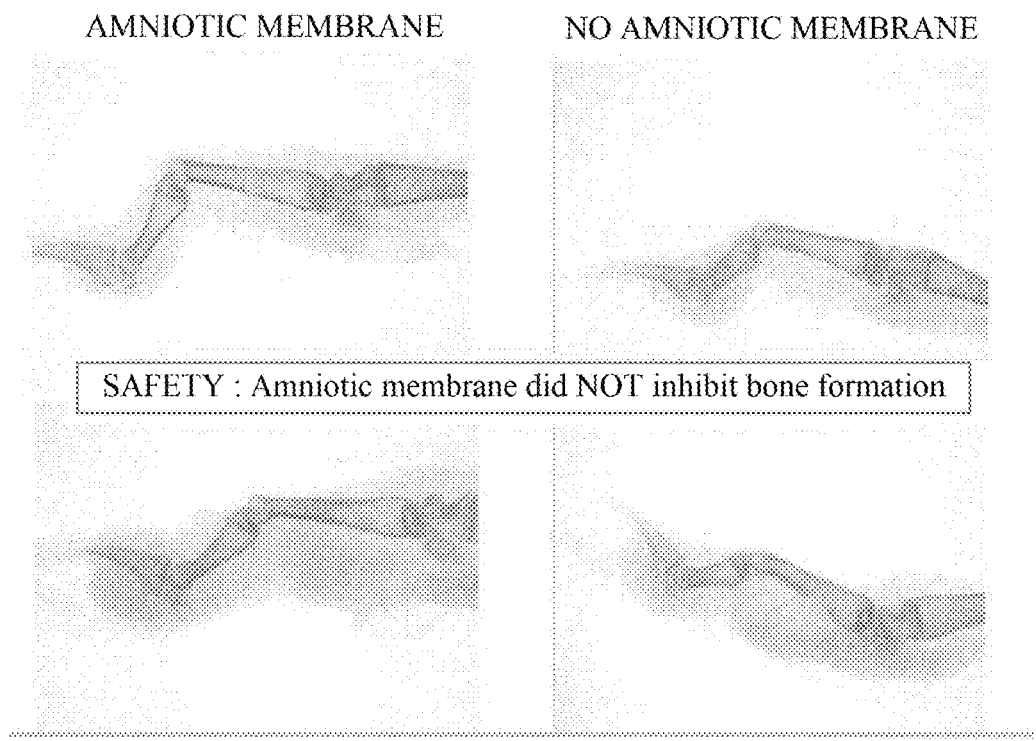
FIG. 5 is a radiograph of bone formation in fracture joining.

As a result, bone formation was not inhibited even when the medical treatment was performed using the HD amniotic membrane. (FIG. 5).

<Production of HD Amniotic Membrane>

Figure 6:
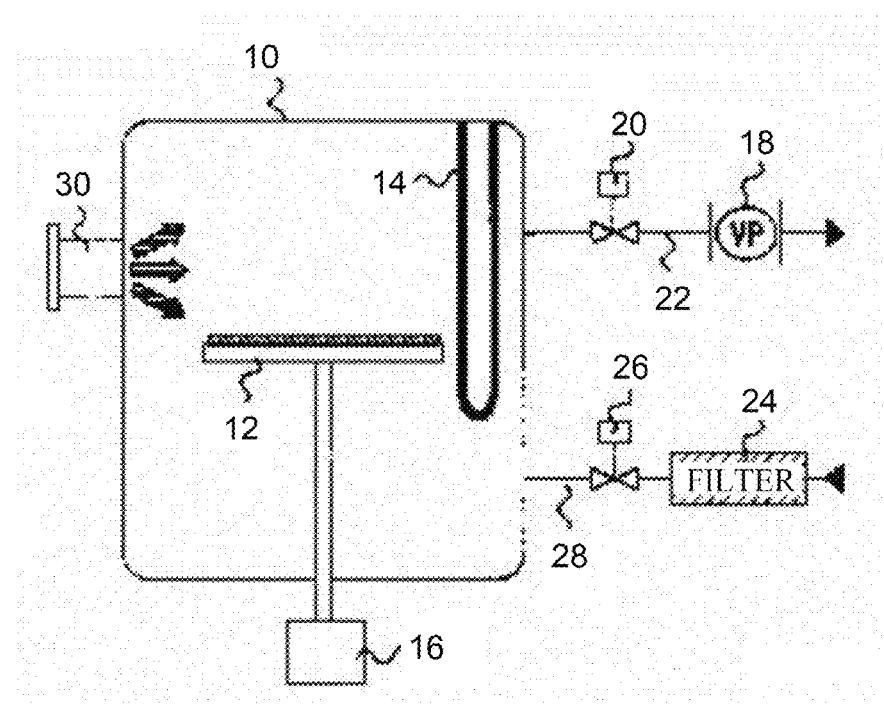
FIG. 6 is a configuration view of an apparatus for producing an HD amniotic membrane.

A fresh amniotic membrane was dried using a drying apparatus shown in FIG. 6 under the following vacuum, far-infrared ray, and microwave conditions.

Drying tank heating: 50° C., F.I.R: 50° C., stop valve: 37%, maximum ultimate pressure: 0.34 kPa, maximum ultimate pressure during idling: 0.33 kPa Drying Treatment Method (1) Depressurization: 180 sec
(2) Pressure recovery: 30 sec (stop valve opening: 37%) Microwave input 0.1 kw, 180 sec (pressure recovery continues)

(3) Depressurization: 180 sec
(4) Thereafter, repeat (2) and (3)
(5) The drying is manually terminated by confirming the ultimate pressure after depressurization for 180 seconds in (3) (0.30 to 0.35 kPa).

The pressure is returned to atmospheric pressure and the drying treatment is completed.

INDUSTRIAL APPLICABILITY

A dried amniotic membrane is produced by performing a specific drying treatment, that is, during a depressurization operation in which a fresh amniotic membrane placed in a treatment tank is continuously heated by an infrared heater provided in the treatment tank, and the inside of the treatment tank is brought into a depressurized state; and a pressure recovery operation in which the pressure of the inside of the treatment tank in a depressurized state is raised slightly toward the atmospheric pressure, drying is performed while applying energy to water molecules present in the amniotic membrane by irradiating the fresh amniotic membrane with a microwave also from a microwave generator provided in the treatment tank. The amniotic membrane dried while retaining the cell and tissue structures by repeating the treatment a plurality of times improves the storage stability and is also easy to handle as a material for transplantation. The dried amniotic membrane promotes regeneration of the motor function of fingers of upper limbs and lower limbs and is useful as a medical material. Further, in a regeneration or restoration medical treatment of a tendon using the dried amniotic membrane, not only adhesion at a site surrounding a sutured tendon is reduced, but also healing at a bone injury site is promoted, and the QOL of a patient is improved.

What is claimed is:

1. A restoration material, characterized in that the restoration material is a dried amniotic membrane, which is used as a regeneration material for a tendon and a tendon sheath and is obtained by subjecting a fresh amniotic membrane wrapping a fetus of an animal including a human, while heating the fresh amniotic membrane to 50° C. by far-infrared rays:
   (1) depressurization for 180 seconds;
   (2) pressure recovery for 30 seconds and microwave irradiation at 0.1 kW;
   (3) depressurization for 180 seconds; and
   (4) repeating of the processes of (2) and (3), and when ultimate pressure after the depressurization in (3) becomes 0.30 kPa to 0.35 kPa, recovering of the pressure to atmospheric pressure to complete a drying treatment,
   wherein the dried amniotic membrane has been dehydrated and dried so that the dried amniotic membrane can be stored in a dry atmosphere in a sterile state, and in which epithelial cells, a basement membrane, and a connective tissue constituting the fresh amniotic membrane are retained in an amniotic membrane resulting from rehydration by immersion in water or a buffer solution, and
   after a completely ruptured tendon accompanied with bone injury is sutured, disposed, as a regeneration material of the completely ruptured tendon, between the ruptured tendon and an injured bone, and repairs the tendon while suppressing adhesion involving a bone at a site surrounding the sutured tendon without inhibiting bone formation at the bone injury part.

2. A restoration method for a tendon and a tendon sheath, characterized by using, as a regeneration material for a tendon and a tendon sheath, a dried amniotic membrane, which is obtained by subjecting a fresh amniotic membrane wrapping a fetus of an animal including a human, while heating the fresh amniotic membrane to 50° C. by far-infrared rays:
   (1) depressurization for 180 seconds;
   (2) pressure recovery for 30 seconds and microwave irradiation at 0.1 kW;
   (3) depressurization for 180 seconds; and
   (4) repeating of the processes of (2) and (3), and when ultimate pressure after the depressurization in (3) becomes 0.30 kPa to 0.35 kPa, recovering of the pressure to atmospheric pressure to complete a drying treatment,
   wherein the dried amniotic membrane has been dehydrated and dried so that the dried amniotic membrane can be stored in a dry atmosphere in a sterile state, and in which epithelial cells, a basement membrane, and a connective tissue constituting the fresh amniotic membrane are retained in an amniotic membrane resulting from rehydration by immersion in water or a buffer solution, and
   after a completely ruptured tendon accompanied with bone injury is sutured, disposed, as a regeneration material of the completely ruptured tendon, between the ruptured tendon and an injured bone, and repairs the tendon while suppressing adhesion involving a bone at a site surrounding the sutured tendon without inhibiting bone formation at the bone injury part.

3. The restoration method for a tendon and a tendon sheath according to claim 2, which is a regeneration material for a tendon sheath.

* * * * *